United States Patent
Olson

(10) Patent No.: US 8,983,589 B2
(45) Date of Patent: Mar. 17, 2015

(54) AUTOMATIC MEASUREMENT OF ISCHEMIC LEVELS IN CORONARY SEGMENTS TO DETERMINE ARTERY RESPONSIBLE THEREFOR

(71) Applicant: ECG-Tech Corporation, Huntington Station, NY (US)

(72) Inventor: Charles W. Olson, Huntington Station, NY (US)

( * ) Notice: Subject to any disclaimer, the term of this patent is extended or adjusted under 35 U.S.C. 154(b) by 69 days.

(21) Appl. No.: 13/684,429

(22) Filed: Nov. 23, 2012

(65) Prior Publication Data

US 2013/0131531 A1    May 23, 2013

Related U.S. Application Data

(60) Provisional application No. 61/563,143, filed on Nov. 23, 2011.

(51) Int. Cl.
| | |
|---|---|
| *A61B 5/0402* | (2006.01) |
| *A61B 5/044* | (2006.01) |
| *A61B 5/00* | (2006.01) |
| *A61B 5/04* | (2006.01) |

(52) U.S. Cl.
CPC ............... *A61B 5/044* (2013.01); *A61B 5/743* (2013.01); *A61B 5/04012* (2013.01)
USPC ......................................................... 600/512

(58) Field of Classification Search
USPC .......................................... 600/512, 523–525
See application file for complete search history.

(56) References Cited

U.S. PATENT DOCUMENTS 5,819,741 A * 10/1998 Karlsson et al. .............. 600/523

OTHER PUBLICATIONS

Olson, Charles W., et al., Olson method for locating and calculating the extent of transmural ischemic areas at risk of infarction, Journal of Electrocardiology 47 (2014) 430-437.
Strauss, David G., et al., Vectorcardiogram Synthesized From 12-Lead Electrocardiogram to Image Ischemia, J Electrocardiology 2009; 42(2), pp. 190-197.

* cited by examiner

*Primary Examiner* — George Evanisko
(74) *Attorney, Agent, or Firm* — John F. Vodopia

(57) ABSTRACT

A method for localizing ischemia in segments of a heart in a patient under test includes attaching a plurality of electrodes to the patient to form a plurality of leads, capturing electric signals at each of the leads, determining a normalized vector magnitude for each lead as is inherent in a normal heart, calculating an output for each cardiac segment as a percentage of the left ventricle (LV) by adding up the contributions for all of the leads in the direction of each segment at the J point based on the normalized vector magnitudes and a correct calibration factor for conversion to the percent of LV and taking a dot product of each lead vector and each segment vector to identify a normalized response for each lead at each segment center and using the dot products to multiply the ST J-point signal for each lead.

10 Claims, 22 Drawing Sheets
(9 of 22 Drawing Sheet(s) Filed in Color)

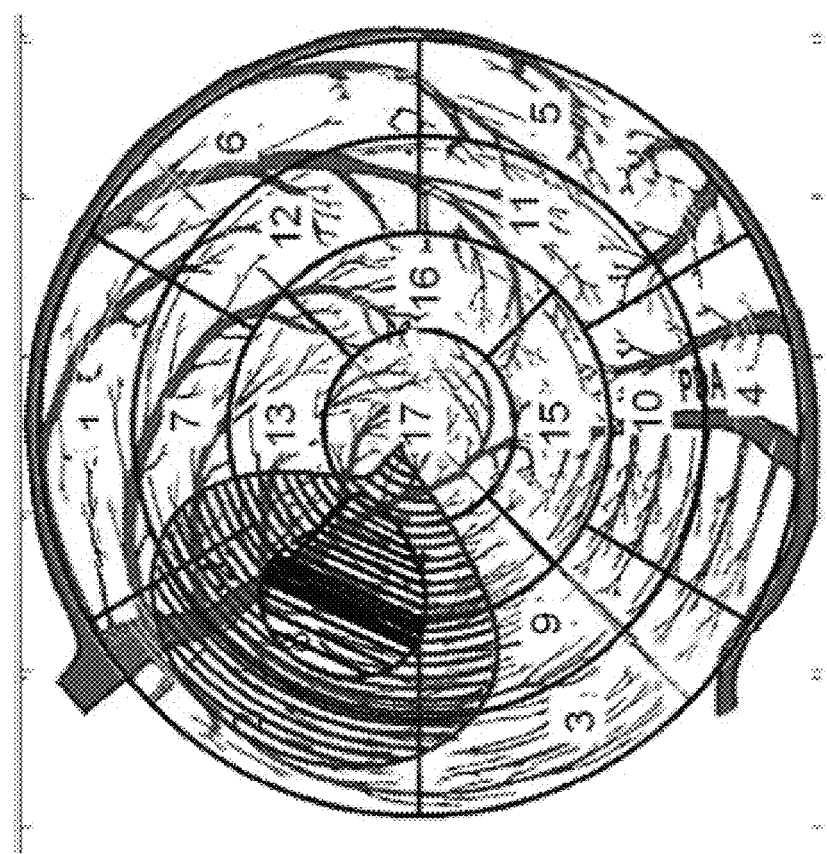

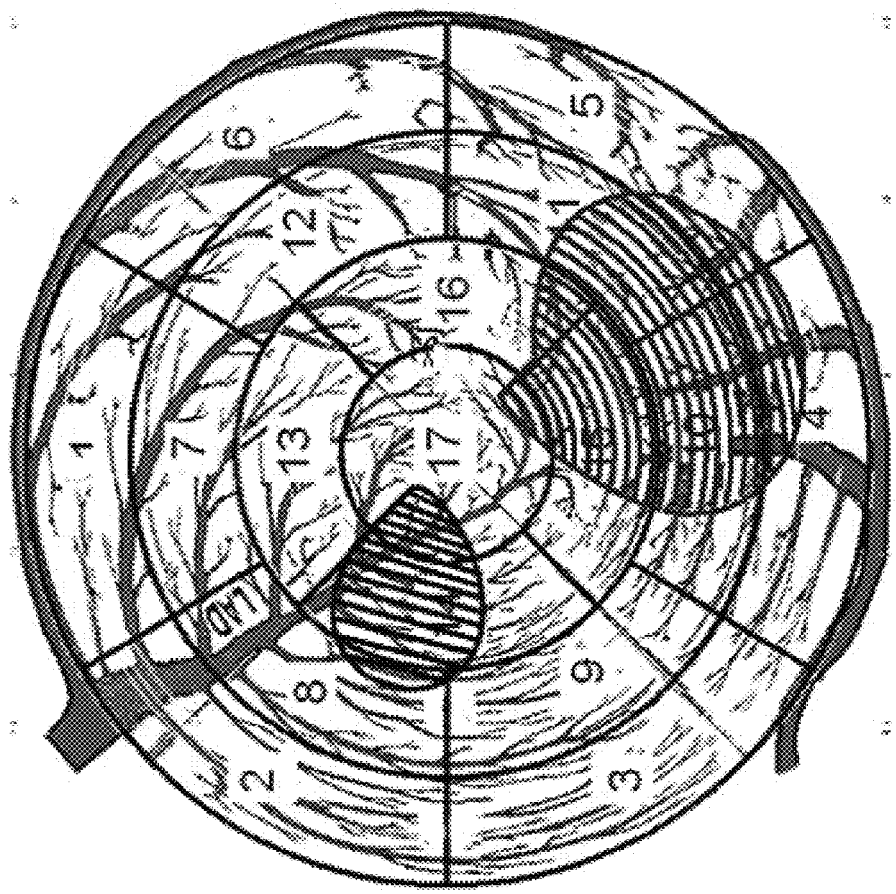

US 8,983,589 B2

AUTOMATIC MEASUREMENT OF ISCHEMIC LEVELS IN CORONARY SEGMENTS TO DETERMINE ARTERY RESPONSIBLE THEREFOR

CROSS-REFERENCE TO RELATED APPLICATIONS

The invention described and claimed hereinbelow claims priority under 35 USC §120 from U.S. Provisional Patent Application 61/563,143 filed Nov. 23, 2011, which is incorporated by reference herein.

BACKGROUND OF THE INVENTION

Systems and methods for analysis of ECG signals are known. For example, U.S. Pat. No. RE 43569 to Olson discloses methods for identifying ischemia conditions/cardiac infarction by analysis of ECG vector signals. Systems and methods that analyze ECG (vector) signals to simply and accurately localize cardiac volumes or segments in which a coronary vessel likely responsible for an ischemic condition are heretobefore unknown.

When the blockage in a single coronary artery occurs it has been found that the location of that coronary artery tree can be associated with the loss of circulation in a selected number of segments of the heart. The inventive systems and methods described herein operate to automatically measure ischemic levels in cardiac segments to determine which coronary artery or segment thereof is responsible for the ischemia and to provide a visual presentation of the heart that clearly and readily identifies the ischemic and/or infarcted area or areas.

The relationship between vectors and heart segments was originally explored by Olson, C W, Warner R A, Wagner G S, Selvester R H S, A DYNAMIC THREE-DIMENSIONAL DISPLAY OF VENTRICULAR EXCITATION AND THE GENERATION OF THE VECTOR AND ELECTROCARDIOGRAM, J. Electrocardiology 2001, 34 (Suppl), pp. 7-15, 2001 (Olson, et al.); R. S. Selvester, G. S. Wagner. R/E. Ideker, "Myocardial Infarction" Chapter 16 "Comprehensive Electrocardiology," p. 565 (1989); and is pictured in a Mercator projection of the left ventricle (FIG. 1). That is, FIG. 1 provides Mercator projection diagram of the Left Ventricle separated into 12 segments. The vertical or ordinate axis is segmented in millimeter (mm) to depict the vertical dimension. The horizontal or abscissa axis extends 360 degrees (azimuth) from −180 to 180 degrees (with reversal at −135 degrees), to depict the surface of the epicardium in a 2D projection.

This Mercator projection diagram highlights that there are 3 main coronary arteries, Left Anterior Descending (LAD), Left Circumflex (LCX) and Right Coronary Artery (RCA). Each of these coronary arteries profuse a chain of segments of the heart, i.e., segment numbers 1-12 (see FIG. 1).

Identifying the ischemic segments, i.e., the segment or segments affected by a blockage of one of these coronary arteries leads to identification of the responsible (blocking) coronary artery as well as the extent and region of the blockage and possible damage to the heart tissue in the segment or segments that is/are nourished by the blocking artery. Such critical information is used to determine the treatment required at an early stage and, therefore, lessen the damage done to the cardiac tissue as a result of the blockage/ischemia.

The quickest and easiest way to recognize an ischemic event is through the use of the Electrocardiograph (ECG). Hence, ECG analysis is one of the first diagnostic tests that are administered in an ambulance, helicopter, etc. (e.g., by a first responder) for a patient with suspected heart attack.

The lead system that is most prevalent in ambulances and hospitals is the 12 lead ECG although the principles applied here could be applicable to other lead arrangements. Many years ago, Ernest Frank, PhD, disclosed a method of measuring the image surface of the homogenous human torso. Dr. Frank started with a model of the human torso and divided it into 12 horizontal slices, as shown in FIG. 2. Dr. Frank took points on the torso in horizontal slices at 2" spacing, number 1-12. Each slice is a cross section, where each cross section also is split or divided into pie sections from the center that have a 22.5 degree radial dimension. To use the Frank model, electrodes are attached at each point of the torso as determined from these cross sections (i.e., volumetric segments). Measurements of the voltage are made at each point on the torso in response to a unit current dipole located at the electrical center of the heart as determined from the torso geometry. The torso is filled with a conducting fluid to simulate the body tissue characteristics. The techniques are described in detail in the paper, Frank, E. "The image surface of a homogeneous torso", Am Heart J. 47:757 1954; Milan Horacek "Lead Theory", Chapter 10 "Comprehensive Electrocardiology" p. 291-314, (1989); MacFarlane, P. "Lead Systems" Chapter 11 "Comprehensive Electrocardiology" p 315-352. MacFarlane also showed that other locations on the heart may be used as a source for the dipole as may be related to the location of the ischemia; MacFarlane, P, Veitch Lawrie; "Comprehensive Electrocardiology" Volume I, Pergamon Press New York (1989).

From the measurement of the voltages at each point on the body, a contour of each of the 12 slices (image surfaces in the horizontal plane) is/was created for the horizontal plane, as shown in FIG. 3. The measurement of the voltage at each of the points on the surface give the contours for each level as numbered. These points at each level are plotted with the letters showing the horizontal angular locations. The lead vectors for the precordial leads are shown on the diagram and give the magnitude and direction of the response of each lead from the torso surface to the Wilson terminal near the center.

The resultant contour is called the image surface and is extremely useful for finding the direction vectors between points on the body or from any point to the Wilson central terminal, which is indicated. Please note that Wilson terminal was explained in: Peter Macfarlane, "Lead Systems" Chapter 11 "Comprehensive Electrocardiology" (p. 315).

SUMMARY OF THE INVENTION

The present invention overcomes the shortcomings of the known arts, such as explained hereinabove.

The invention enables emergency personnel or clinicians, after first identifying that an ischemic event has occurred, to automatically identify the region of ischemic damage, greatly improving patient treatment.

the ability to accurately identify an ischemia and the segment in which ischemic tissue/a blocked coronary artery is located in a patient being transported to a hospital for emergency treatment is invaluable to the decision makers (e.g., electro physiologists) readying to treat the patient under transport (for example, emergency room personnel, electrocardiologists, etc.). Identifying that a STEMI patient is being transported to a hospital emergency room by ambulance allows for advance preparation by hospital personnel, e.g., readying a cardiac catheterization lab.

In an embodiment, the invention provides a system for localizing ischemia in a patient under test and presenting a display image representing a location and an amount of ischemia and/or infarction in a segment. The system includes an ECG apparatus connected to a plurality of electrodes attached to the patient to form a plurality of leads and a processor for processing vector signals captured at each of the leads for determining a normalized vector magnitude for each lead, calculating an output for each segment by adding up the contributions for all of the leads in the direction of each segment at the J point based on the normalized vector magnitudes, taking the dot product of each lead vector and the segment vector to identify a normalized response for each lead at each segment center and using the dot products to multiply the ST J-point signal for each lead.

The system determines transmural ischemia, indicating that the patient is having a serious heart attack which left unattended will likely create permanent heart muscle damage or semi-transmural ischemia, indicating that there is a partial blockage of the patient's coronary artery or arteries as happens in a stress test which should be treated before it becomes more dangerous. A normalized vector magnitude for each lead is found by adding the vector magnitudes of each of the lead vectors, and dividing the sum by the number of leads to find an average. Then the average is divided by each of the individual magnitudes to find a normalized amplitude for each lead. A magnitude of the ST signal at the J-point in each of the leads as found from the 12 lead ECG is then multiplied by the normalized amplitude to find the effect of the leads on each of the segments of the heart.

The processor joins the areas of infarction and presents a representation of the joined areas in a Mercator projection or Bulls Eye diagram and determines a location and size of the ischemic area and a degree of risk to the patient as a percent of the Left Ventricle—area at risk (AAR)—when multiplied by the calibration factor. A maximum area for a segment is 8 percent of the total area of the heart, which area is determined from the level of the signal calculated in that segment.

In another embodiment, the invention provides a method for localizing ischemia in segments of a heart in a patient under test. The method comprises steps of attaching a plurality of electrodes to the patient to form a plurality of leads, capturing electric signals at each of the leads, determining a normalized vector magnitude for each lead as is inherent in a normal heart, calculating an amount of ischemia or output for each cardiac segment as a percentage of the left ventricle (LV) by adding up the contributions for all of the leads in the direction of each segment at the J point based on the normalized vector magnitudes and a correct calibration factor for conversion to the percent of LV and taking a dot product of each lead vector and each segment vector to identify a normalized response for each lead at each segment center and using the dot products to multiply the ST J-point signal for each lead. The segment outputs (percentages) are determined by a calibration of prior data into a formula.

That is, the output for each cardiac segment as a percentage of the left ventricle (LV) is determined by a using prior data and a formula derived from the plotting of the prior data against the magnitude of the ST vector to determine this percentage. A display image representing a location on the heart is presented that derives from a combining of segment levels and developing a centralized area in the form of an ellipse that represents the total ischemic and/or infarction levels as a percent of LV for each. The step of determining the normalized vector magnitude for each lead includes adding the vector magnitudes of each of the leads, dividing the sum by the number of leads to find an average and dividing the average by each of the individual magnitudes to provide a uniform response of the leads to the vector signal of the ischemia.

Determining the normalized vector magnitude for each lead includes determining a magnitude of the ST vector in each of the leads and then translates same to segment to calculate a percent of LV at risk in each segment. For that matter, determining the location of the area of the infarction and of ischemia on a Mercator and Bulls Eye diagrams, which areas many be separated or contiguous. The displaying includes displaying the location of the area of the infarction and of ischemia in one of a Mercator diagram, a Bulls Eye diagram and both.

BRIEF DESCRIPTION OF THE DRAWINGS

The file of this patent contains one or more drawing figures executed in color. Copies of this patent with color drawing figures will be provided by the Patent and Trademark Office upon request and payment of the required fee.

For that matter, further features and advantages of the invention will become apparent from the description of embodiments that follows, with reference to the attached figures, wherein:

FIG. 10a depicts segment outputs for 25 patients with known RCA ischemia;

FIG. 15B depicts a Bull's Eye diagram for a patient with both an infarct and ischemia event in the LAD region;

FIG. 16B depicts a Bull's Eye diagram for a patient with both an infarct in the LAD region and ischemia event in the RCA region

DETAILED DESCRIPTION OF THE PREFERRED EMBODIMENTS

The following is a detailed description of example embodiments of the invention depicted in the accompanying drawings. The example embodiments are presented in such detail as to clearly communicate the invention and are designed to make such embodiments obvious to a person of ordinary skill in the art. However, the amount of detail offered is not intended to limit the anticipated variations of embodiments; on the contrary, the intention is to cover all modifications, equivalents, and alternatives falling within the spirit and scope of the present invention, as defined by the appended claims.

Figure 2:
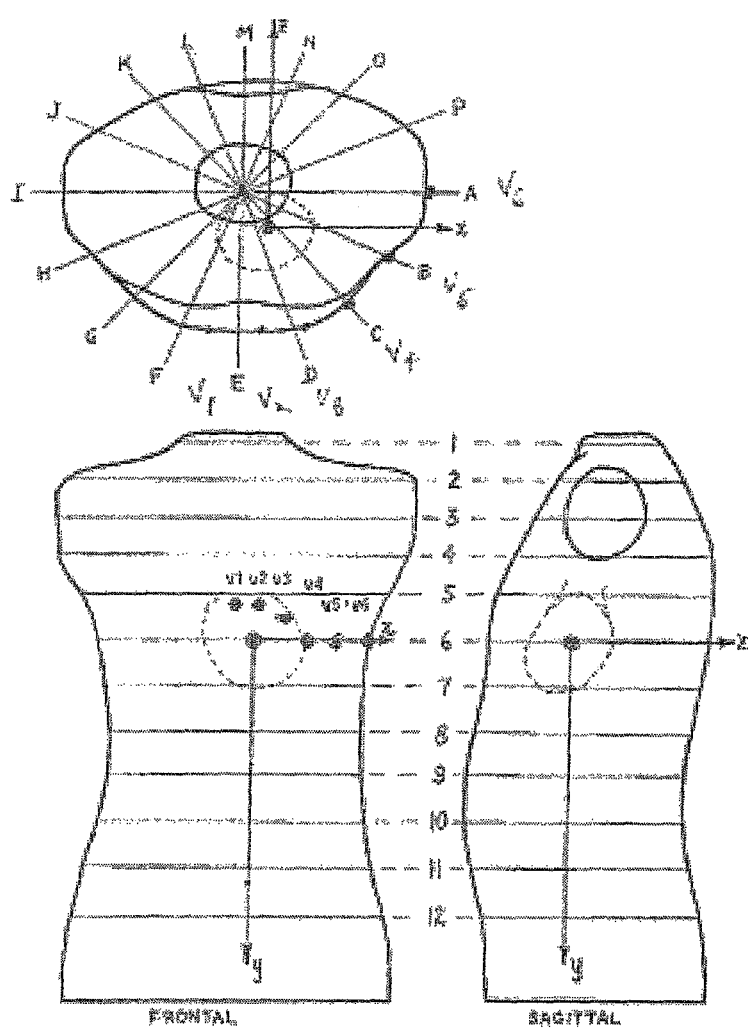
FIG. 2 depicts Frank Torso measurement points, as is known.
Figure 3:
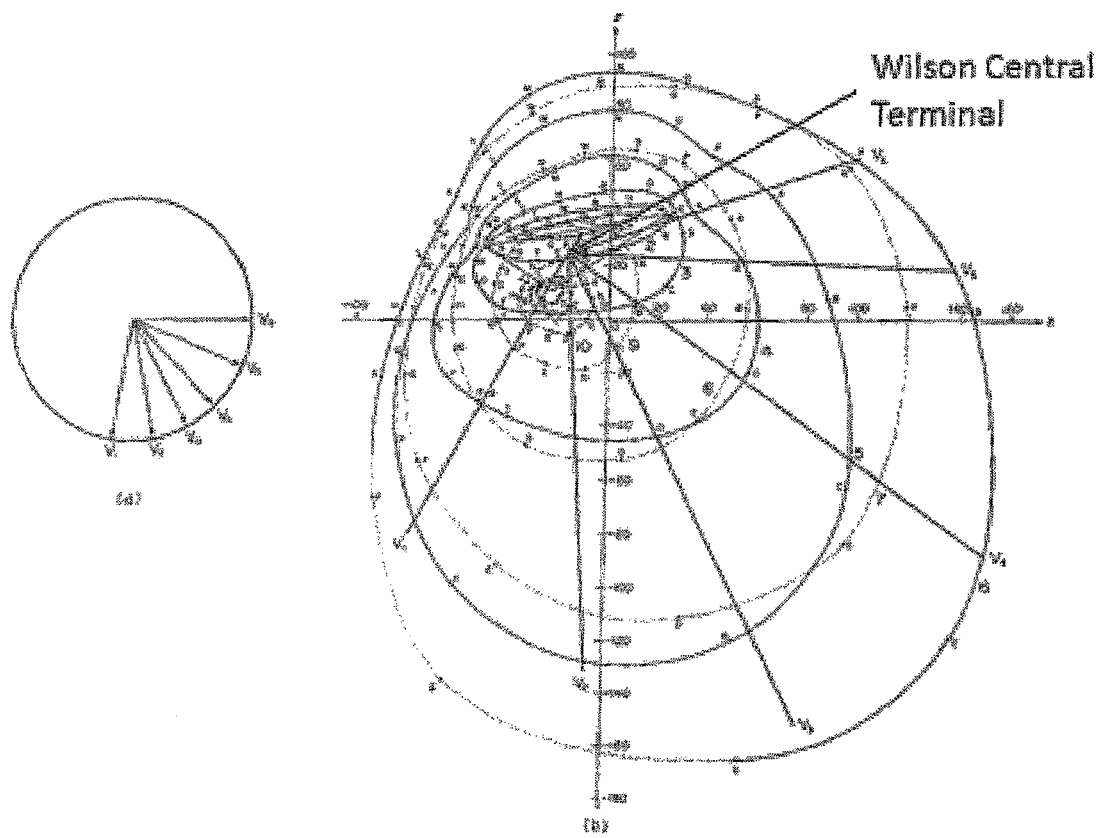
FIG. 3 depicts image surfaces in the horizontal plane, as is known.

In FIG. 2 the physical location of the precordial leads are shown as normally used in a 12 lead ECG, at the Frank torso measurement points. In FIG. 3, each of the precordial leads—V1 to V6—are shown from their respective points on the torso to the Wilson central terminal. Image surface from the horizontal cross-sections as mentioned in Frank and pictured in McFarlane, who added lead vectors V1-V6. The starting points on the torso for leads V1, V2 and V3 are interpolated between the levels/slices 5 and 6 (as seen in FIG. 2). The remainder of leads, V4, V5 and V6, start at the level/slice 6. The length and direction of each of these leads gives dimensions in the coordinates "x" and "z."

By adding a frontal plane diagram, a "y" dimension is added to each of the leads. The Limb leads are longest in the frontal plane because the points of attachment to the body are located on the arms and the legs. The "I" lead is measured between the left and right arm with the plus terminal the left. The "II" lead is measured between the left arm and the left leg and the "III" lead between the right arm and the left leg. It was initially thought that the orientation of these leads formed an equilateral triangle with the top leg between the arms and the other two legs, from these points to the middle of the body near the bottom of the torso.

Figure 4:
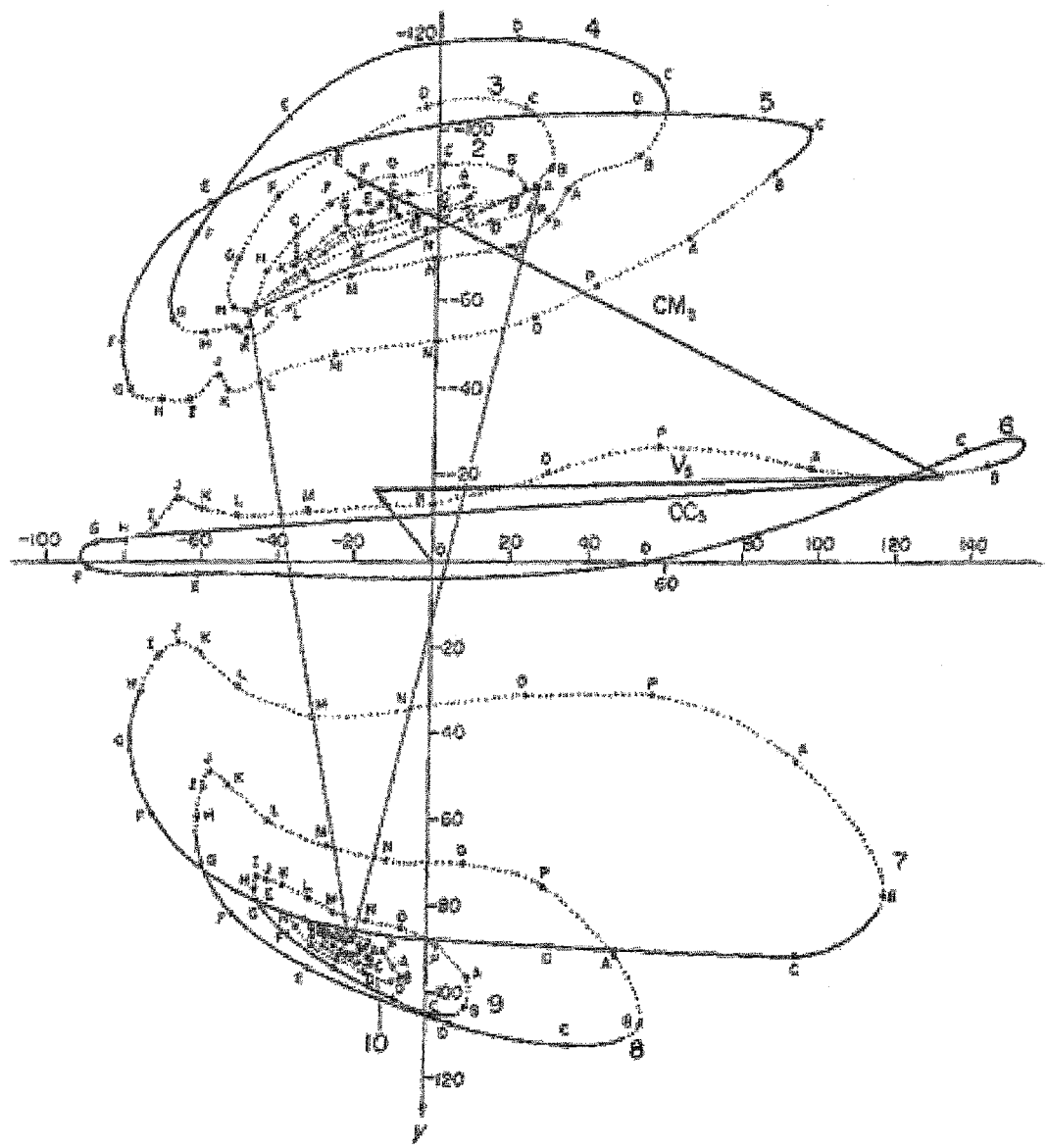
FIG. 4 depicts image surfaces in the frontal plane view, as is known.

The true orientation of this triangle is shown in FIG. 4 and used in the system and method disclosed herein along with the derived leads (as shown in FIG. 3). The invention uses these leads, i.e., the signal and direction to derive responsiveness of the lead. In FIG. 4, the same electrical measurement contours for each of the horizontal levels is shown in the frontal plane. These contours/data allows the plotting of the lead vector response of the limb leads as well as the precordial leads. The limb leads form what is called the burger triangle showing the lead vector response of leads I, II and III. For this triangle, the response of the leads aVL, aVR and aVF also may be derived and are shown in this figure.

Normalized Vectors Derived from 12 Leads

The ECG vectors measured from the Frank diagrams are in 3 dimensions—x, y, and z. As used herein, the term "vector" means the magnitude and direction of an ECG signal captured by an ECG machine in either analog or sampled form. These vectors are distributed at about 30 degree increments in the frontal and horizontal planes. With the ability to measure both plus and minus voltages on each of the leads, there is 360 degree coverage by these leads in the 2 planes.

Figure 5:
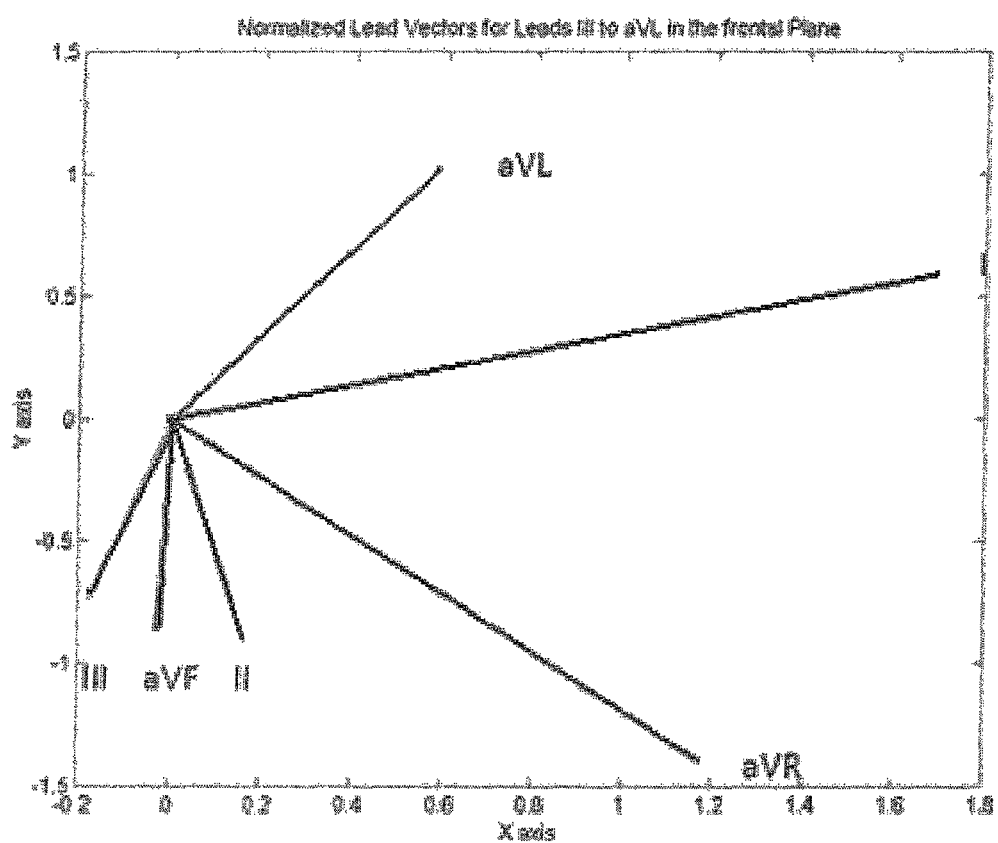
FIG. 5 depicts normalized lead vectors for leads III to aVL in the frontal plane.
Figure 6:
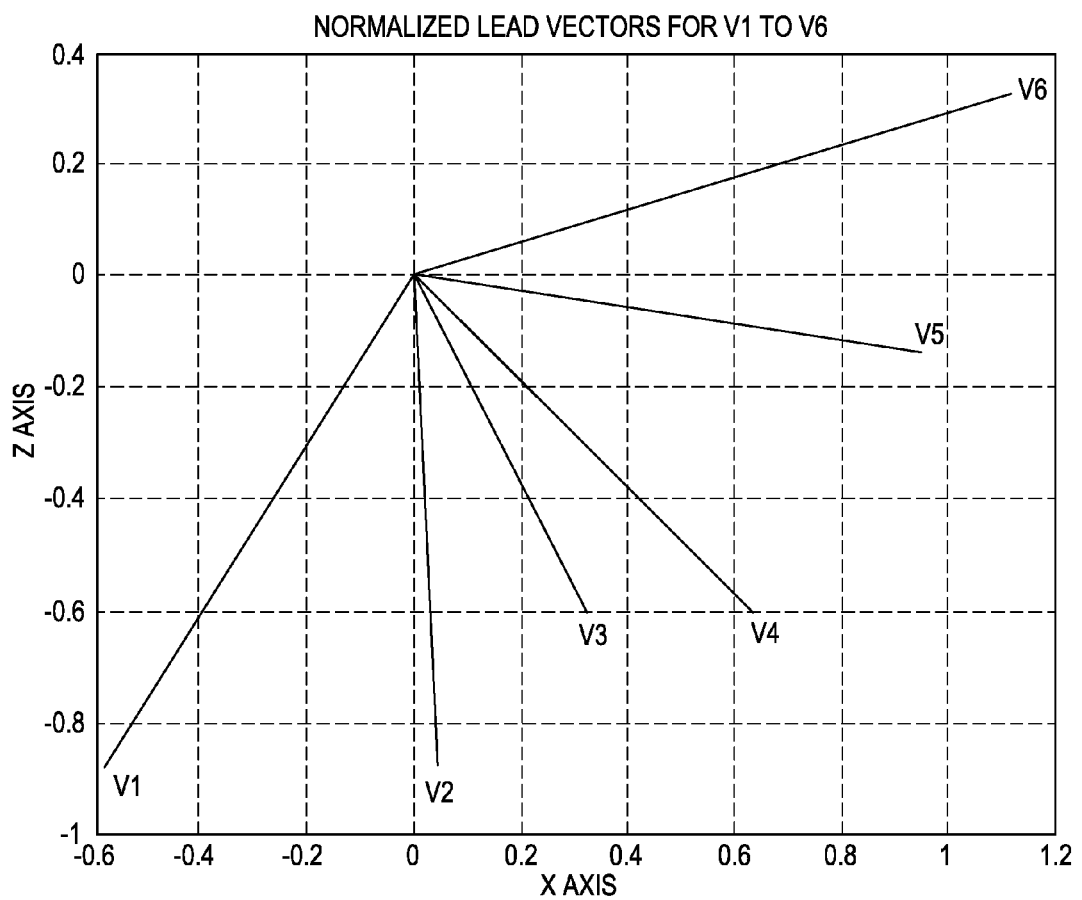
FIG. 6 depicts normalized lead vectors for leads V1 to V6.

The inventive system and method finds the average vector magnitude of all the leads. Then to accomplish the normalization, the average magnitude is divided by each of the individual magnitudes. This deemphasizes strong leads and emphasizes weak leads, Thus, no matter the direction of the vector to be measured, the same response would be found at the output of the sum of these normalized vectors. The direction and magnitude of these normalized lead vectors in the frontal and horizontal planes is shown in FIGS. 5 and 6, respectively. Each of the lead vectors is defined in 3 dimensions, although the magnitude of the response in the orthogonal axis for the vectors shown is minimal.

Vectors were Found at the Centers of Each Segment

Figure 7A:
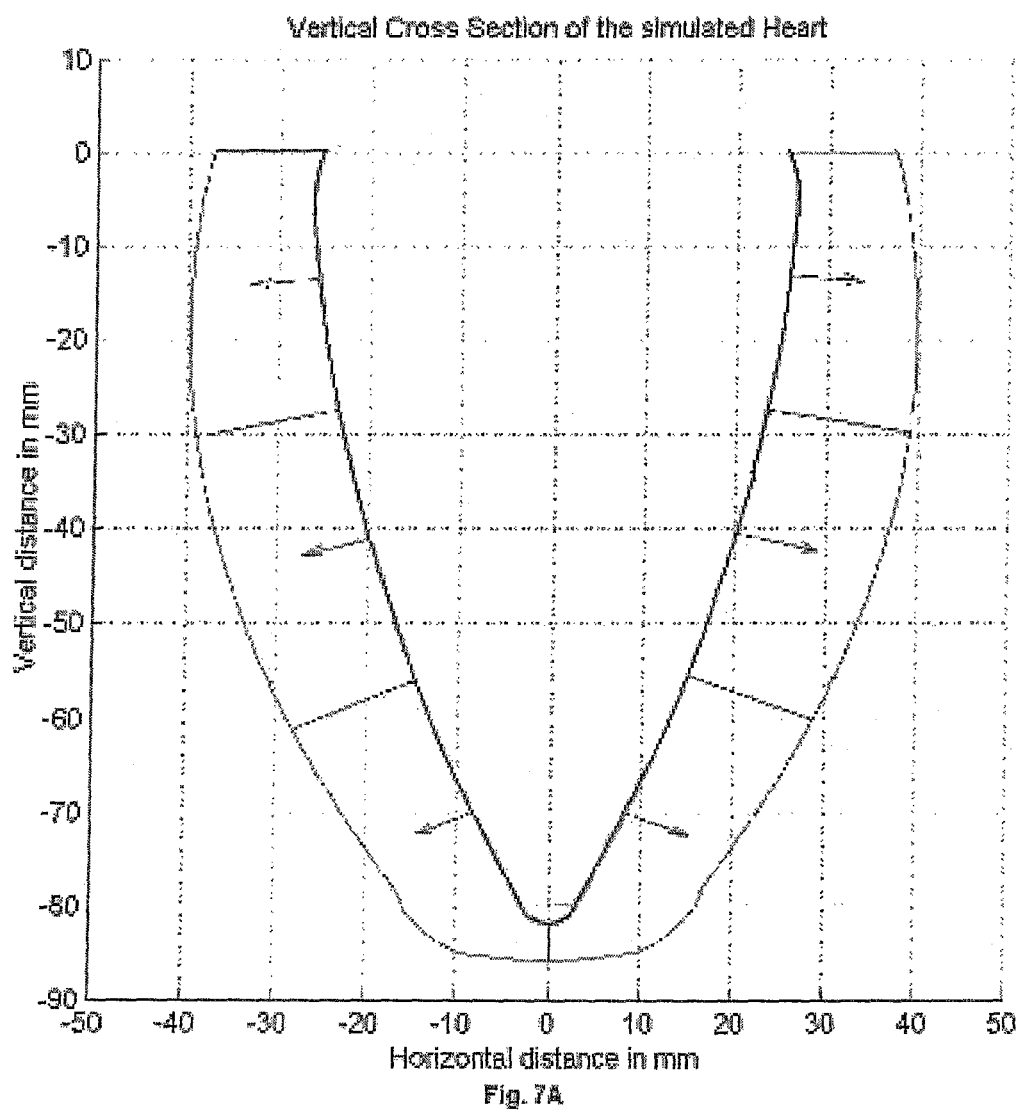
FIG. 7a depicts the unit vectors for each segment in the horizontal plane representing the direction of the ischemic vectors at one of three levels.
Figure 7B:
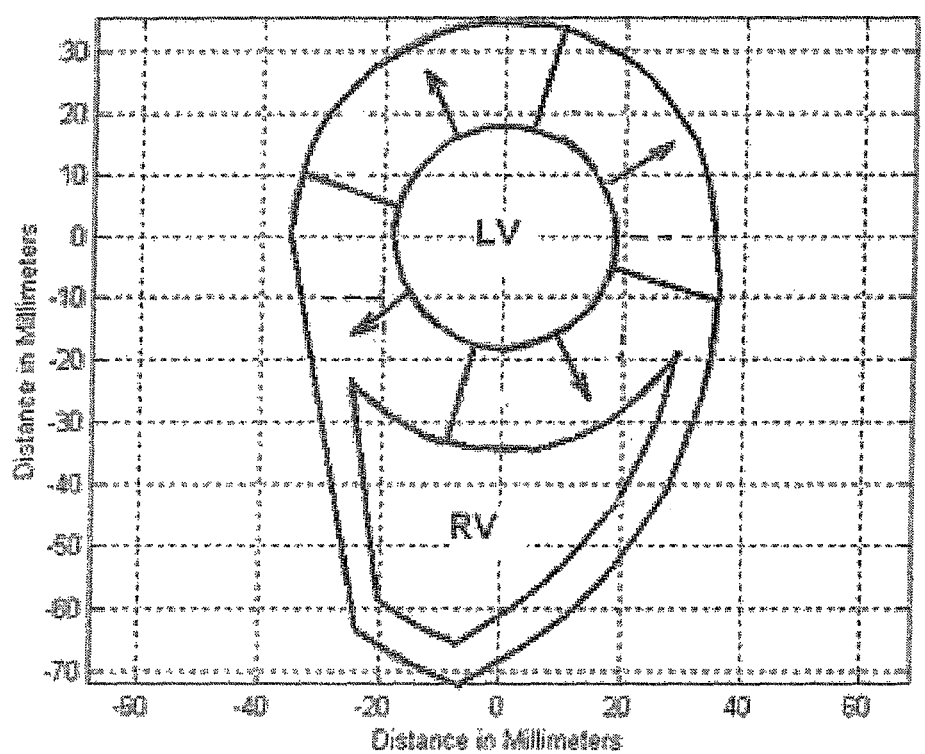
FIG. 7b depicts the unit vectors for each segment in the vertical plane representing the direction of the ischemic vectors at one of the 2 cross sections that apply.

A model of the heart previously developed by the inventor herein and disclosed in Olson, et al. is used in a simulation program in which vector directions were established at 1 mm spacing. A realistic model of the heart was also defined at 1 mm spacing. In FIGS. 7A and 7B, cross sections of the heart model are presented. At the centroid of each quadrant, a vector pointing perpendicular to the endocardial surface of the Left Ventricle is depicted. This vector direction is obtained by taking the cross product of orthogonal vectors in the plane of the surface at each point (on a Frank torso as shown in FIG. 2). The centroid is obtained by bisecting the vertical spread of the vertical opening and the angular spread of the horizontal opening for each segment. The vertical opening is 28 mm and the horizontal opening is 90 degrees. Centroids of segments are shown in FIG. 7A where FIG. 7B depicts centroids of quadrants.

Also shown are the location of the vectors at the centroid of each segment which is determined geometrically as the central point for each dimension on the endocardium. The vector direction is found by taking the cross product of surface vectors at their point of origin. Thus, by selecting a location that is at the centroid of each of the segments on the endocardium, a vector direction is known and can be used as a good representation of the vector that would occur in the event the segment was ischemic. It is known that the potential on the endocardium is high since these muscle cells are well profused by the blood in the inside of the Left Ventricle. As the ischemia develops, the cells in the middle and on the epicardium suffer loss in Action Potential due to loss of profusion. The resultant vector points away from the endocardium and towards the epicardium when the ischemia extends across the thickness of the cross section (transmural ischemia).

Figure 7C:
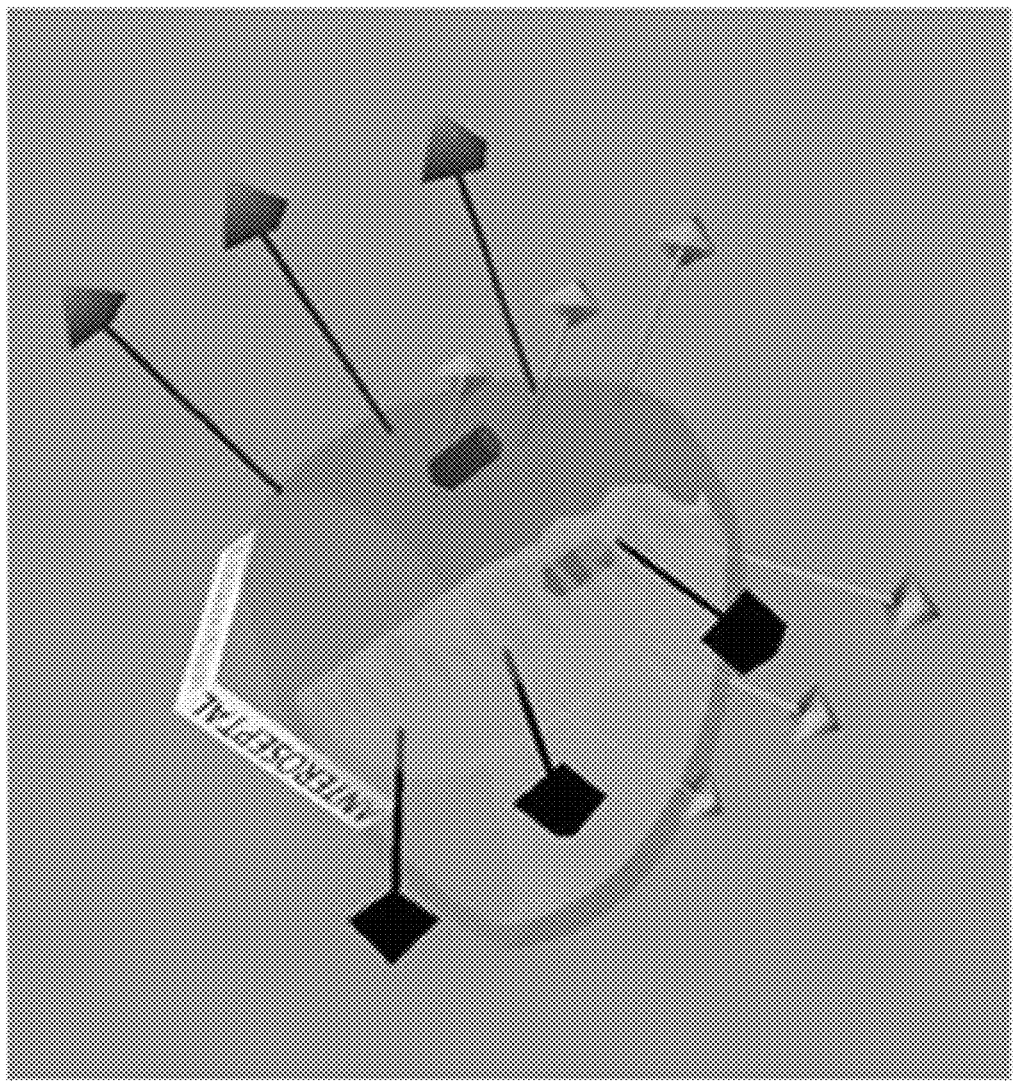
FIG. 7c depicts the unit vectors for each segment in a 3D drawing representing the direction of the ischemic vectors.

The direction vector, as described above, is used to represent the average for each of the 12 segments. Examples of these for the 12 segments of the LV are shown in FIG. 7C. That is, FIG. 7C shows the unit vectors for each segment representing the direction of the ischemic vectors. The unit vectors representing anteroseptal are black from 1 to 3 with 1 apical; the anterosuperior are green from 4-6 with 4 apical; the posterolateral are blue from 10 to 12 with 10 apical; and the inferior are purple from 7 to 9 with 7 apical.

These vector directions represent the case of transmural ischemia. In the case of semi transmural ischemia (such as in a stress test), only the inner part of the myocardium is ischemic. As a result the reference vector for each segment points in the opposite direction (180 degree difference in phase). Semi transmural ischemia, blood flow is limited in the arteries on the inner surface of the heart and cells in the middle of the epicardium have a longer action potential than what is present on the endocardium. This results in a higher potential in the middle of the cross section after the J point and thus a vector at this time pointing towards the endocardium or the reverse of the direction depicted in FIGS. 7A, 7B and 7C.

Ischemic Output for Each Segment

The output (i.e., amount of ischemia) for each segment is found by adding up the contributions for all the leads in the direction of each of the segment vectors. In the case of an ischemic event, the best measure of the effect on the lead signal is at the J point. This is the point where the normal activation of the myocardial cells that are not ischemic stops. Each lead shows its response to the sum of the ischemic activity at this point in time (J-point). Each lead has a vector direction and each segment has a vector direction. By taking the dot product of these 2 vectors, a normalized response for each lead at each segment center is found. The contribution of each lead to a segment is the component of that lead in the direction of the segment vector (the dot product of the 2). Since these products are scalars, they each can be multiplied by their respective ST J-point signal for each lead to get their net total contribution to the ischemic level at each unit vector location.

If the sign of the dot product and the sign of the ST signal are the same, their product is used because they indicate transmural ischemia. If the dot product and sign of the ST segment are opposite in sign, a separate sum is calculated indicating semi-transmural ischemia.

Figure 1:
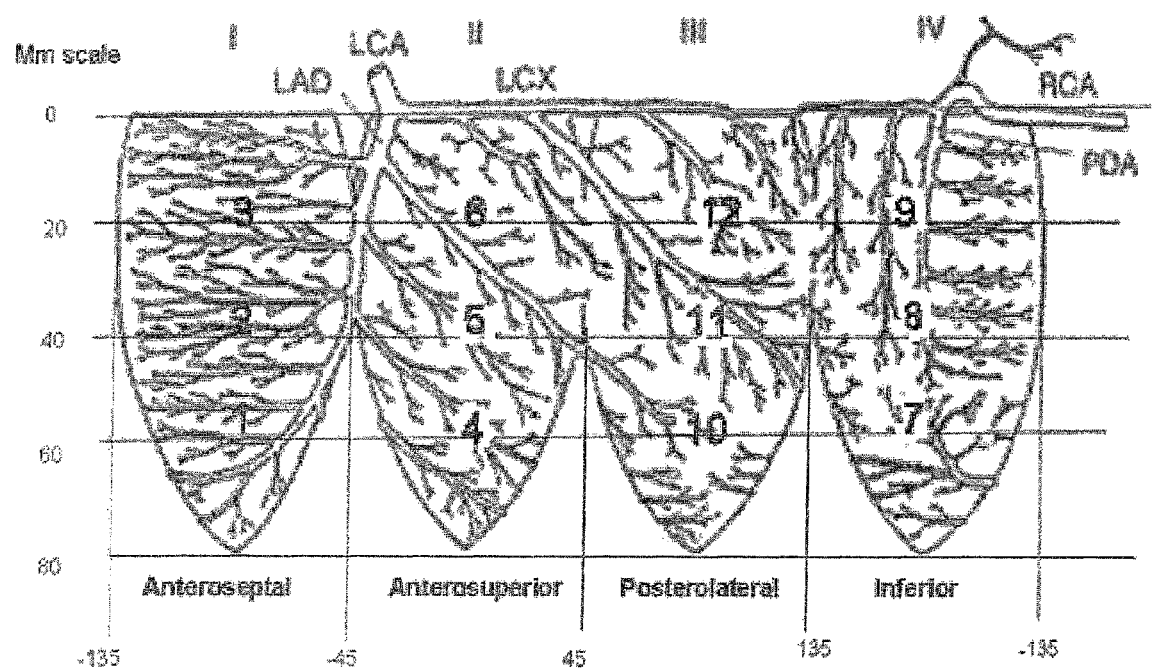
FIG. 1 depicts a Mercator projection diagram of the Left Ventricle showing 12 segments, as is known.
Figure 8:
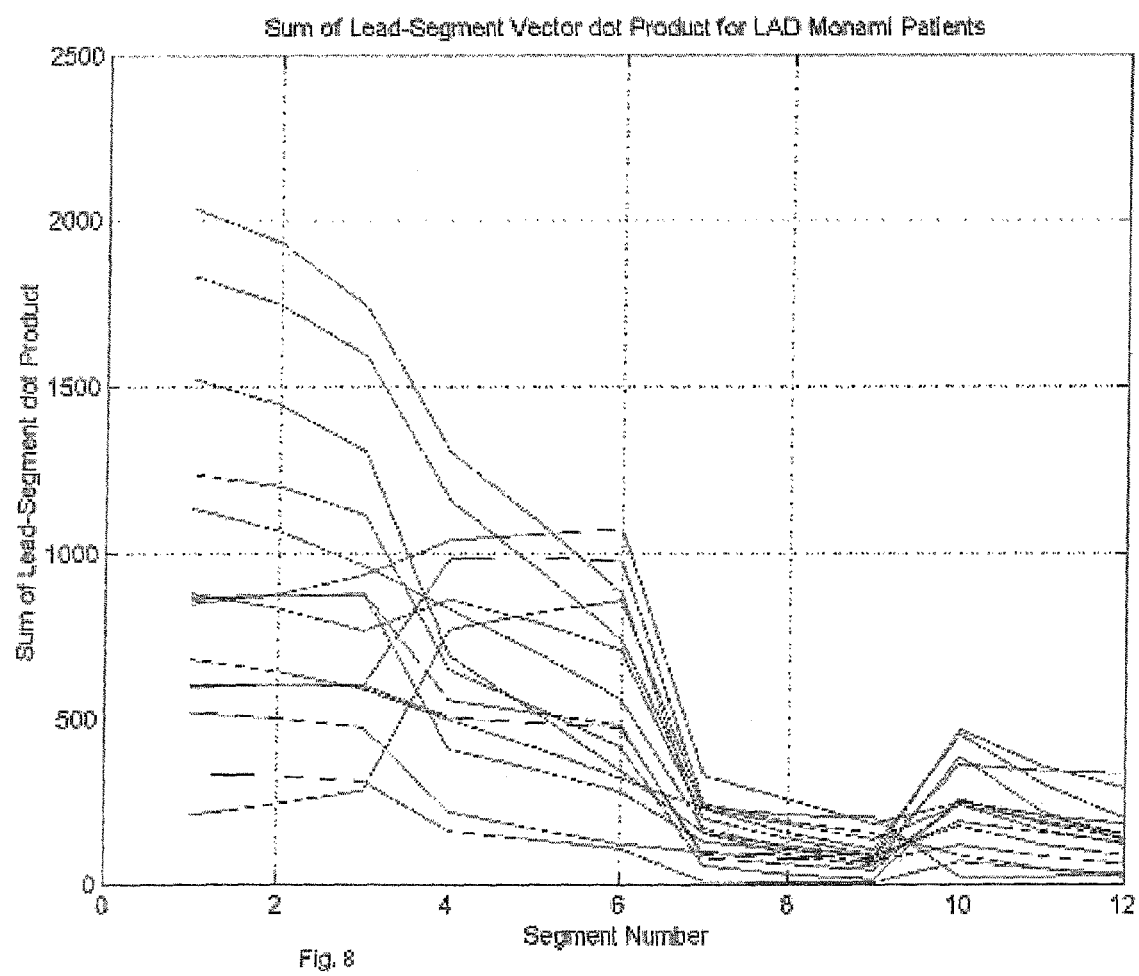
FIG. 8 depicts segment outputs for 29 patients with known LAD ischemia.
Figure 9:
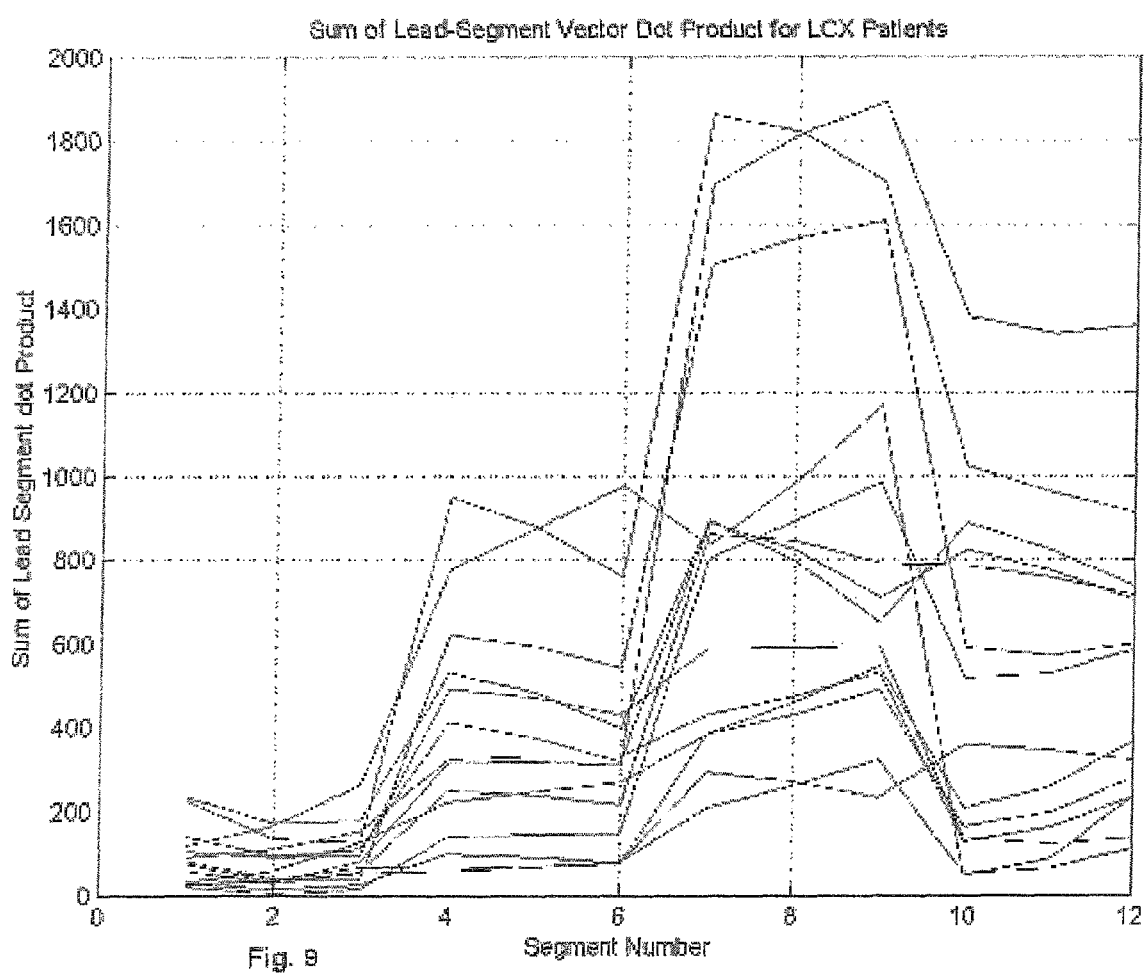
FIG. 9 depicts segment outputs for 15 patients with known LCX ischemia.
Figure 10B:
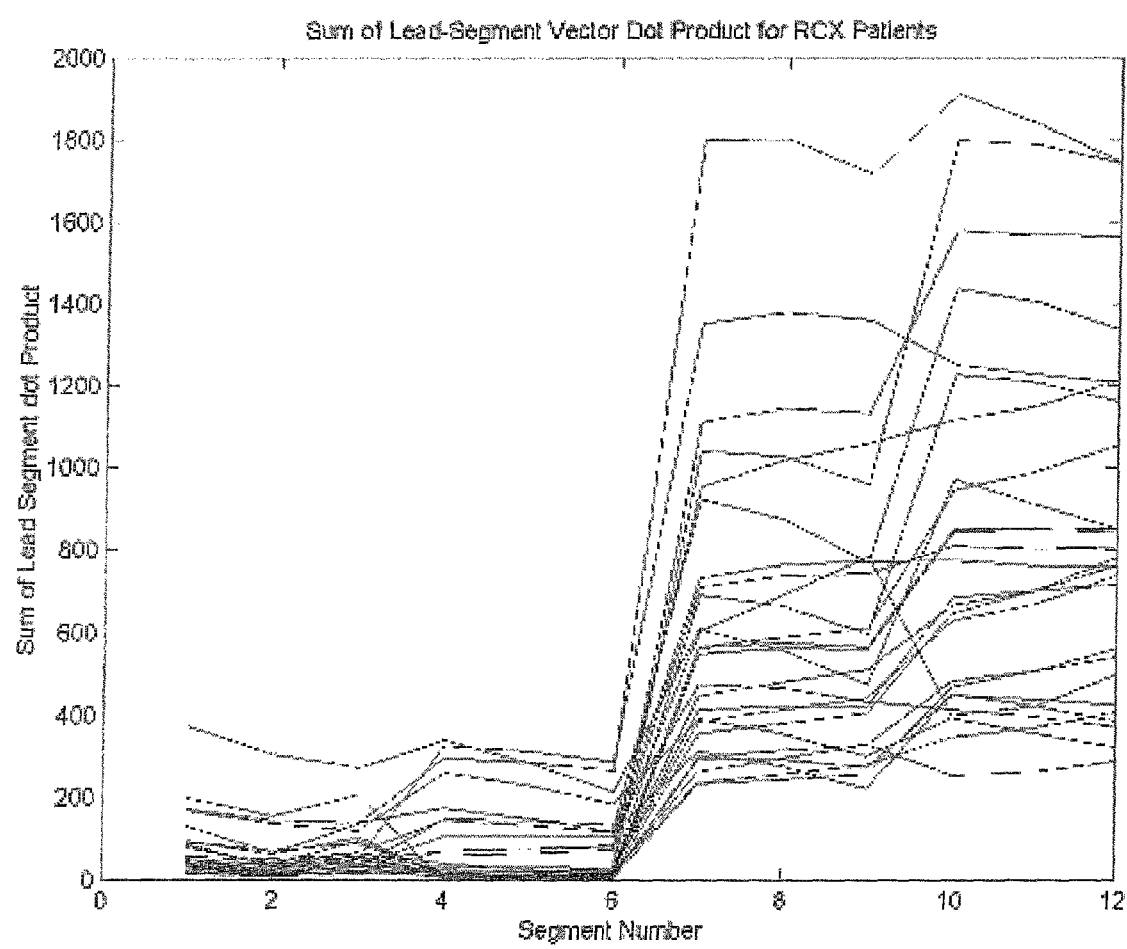
FIG. 10b depicts a plot of patient measurements of the Aldrich score (% LV ischemic) vs. ST-magnitude as measured by the inverse dower transform of the x, y, and z data.
Figure 10B:
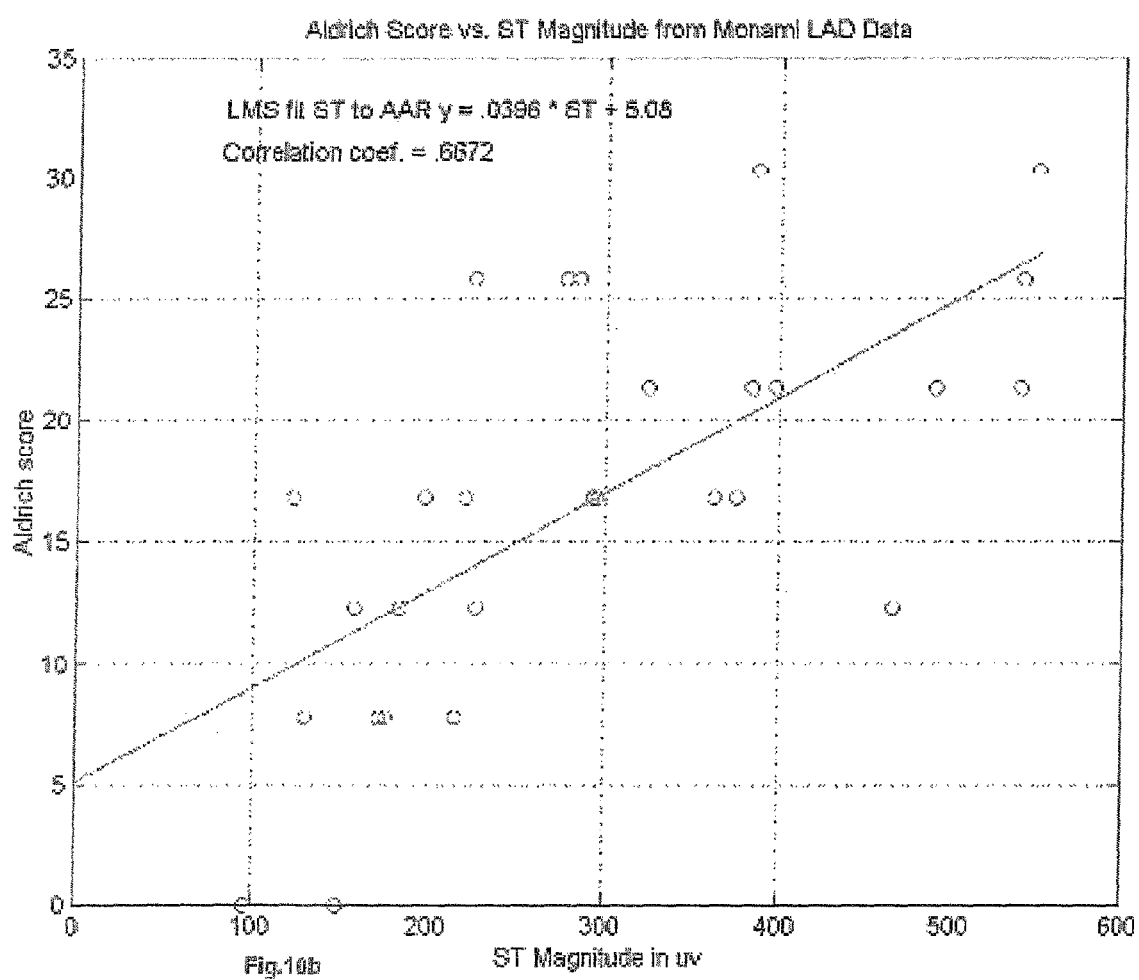

Examples of the plotting of these outputs for each patient of groups separated by their coronary artery affected by the ischemia are shown in FIGS. 8, 9 and 10. FIG. 8 shows LAD patients with near 100 percent correlation with the maximum deflection in segments 1 to 6. FIG. 9 shows LCX patients where 14 out of 15 are found to be correctly classified. In the RCA group in FIG. 10, 14 correct and 10 RCA or LCX, 1 RCA or LAD and 2 LCX are found. Please note that in these plots, the order of segments 7, 8, 9 and 10, 11, 12 were changed, since the physical order is 10, 11, 12 and 7, 8, 9, as shown in the Mercator projection diagram of FIG. 1.

Figure 11:
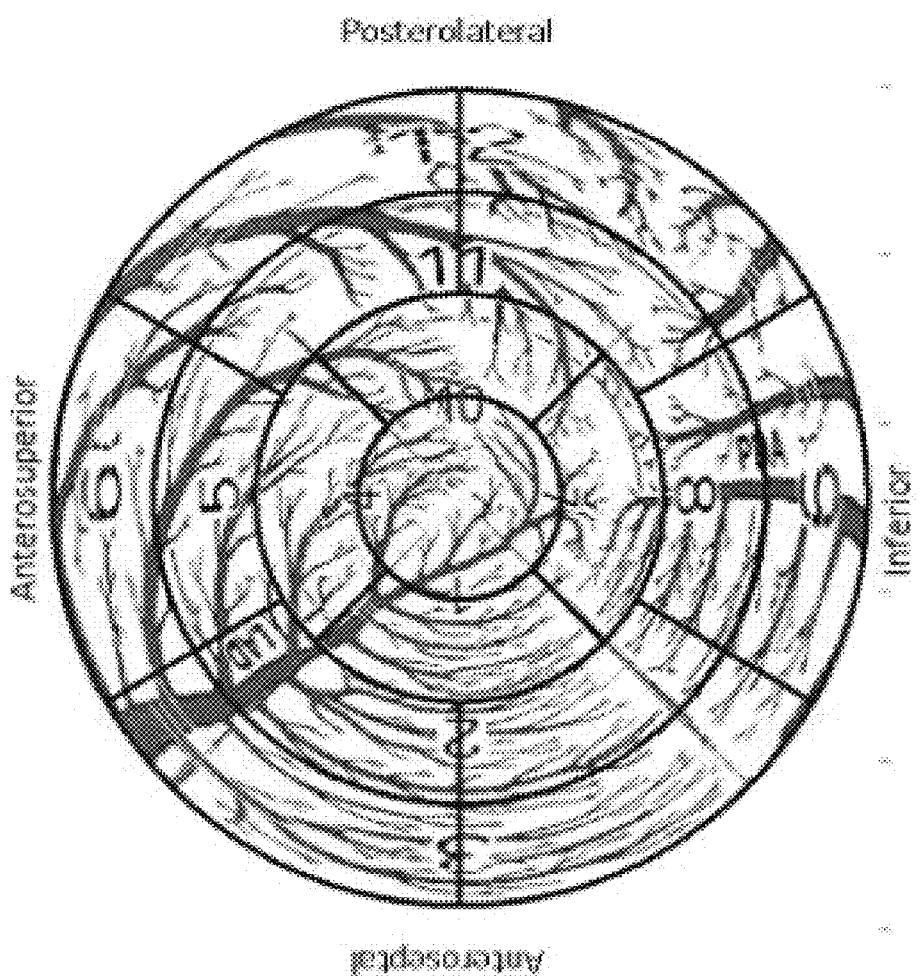
FIG. 11 depicts a Bull's Eye diagram of the left ventricle with the coronary arteries as translated from the Mercator Diagram (17 segment circle diagram)
Figure 12:
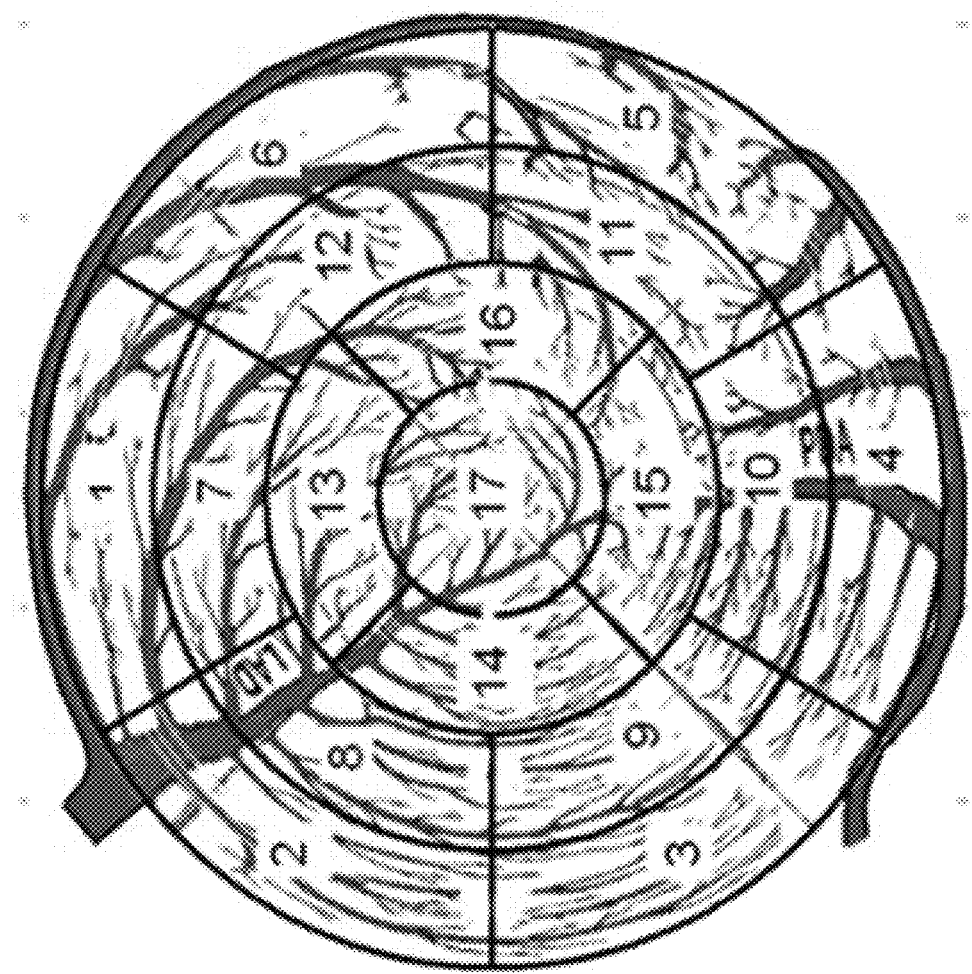
FIG. 12 depicts a Bull's Eye diagram of the left ventricle showing the 17 segments.

Location of the Infarction Output on the Mercator and the 17 Segment Circle Diagram The Mercator projection diagram of the Left Ventricle can be translated to a Bulls Eye representation, as shown in FIG. 11. This shows the location of the coronary arteries in the Bulls Eye diagram by a point by point transformation of the Mercator coronary layout. Quadrants are shown for the Mercator segments and their orientation in the 17 segment circle diagram in FIG. 12. The horizontal lines that are shown in the FIG. 1 Mercator Projection diagram (12 segments) are translated over their active extent to circles in the Bulls Eye diagram of FIG. 11. The outer circle represents the top line in the Mercator diagram and bottom or the tip of the apex of the heart is the center of the bull's eye. This translation is shown for each quadrant and the coronary arteries are arranged in relationship to their geometric translation. The more preferred numbering of the Bulls Eye segments and their arrangement is shown in FIG. 12, the 17 segment model.

In the event of the infarction of the Left Ventricle, Sylvester, et al., have shown that the amount of infarction in each segment can be estimated from the 12 lead ECG characteristics. These segments are normally adjacent to each other and arranged in accordance with the type of infarction. LAD infarction is found to exist in one or more of the segments 1 to 6, 7, and 10. RCA infarction is found to exist in segments 7 to 9 and LCX is found to exist in segments 10 to 12 (according to Sylvester). The inventive system and method create a new elliptical area (in the Mercator that represents the area at risk in percent of the Left Ventricle.

Figure 13:
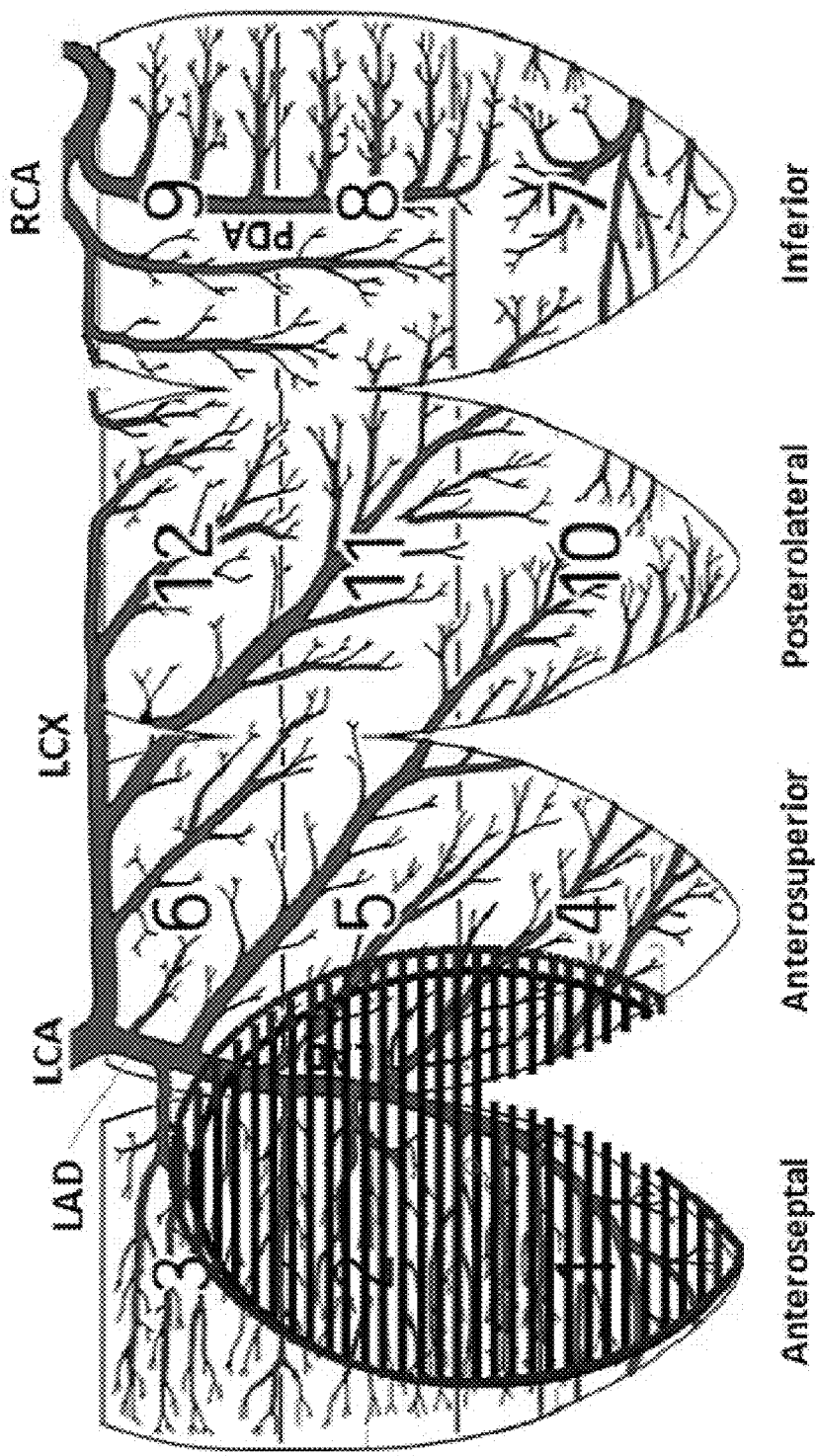
FIG. 13 depicts a Mercator Projection of the left ventricle showing 4 quadrants with ischemic views outlined in pink or in shadow and infarcted areas outlined in black.
Figure 14:
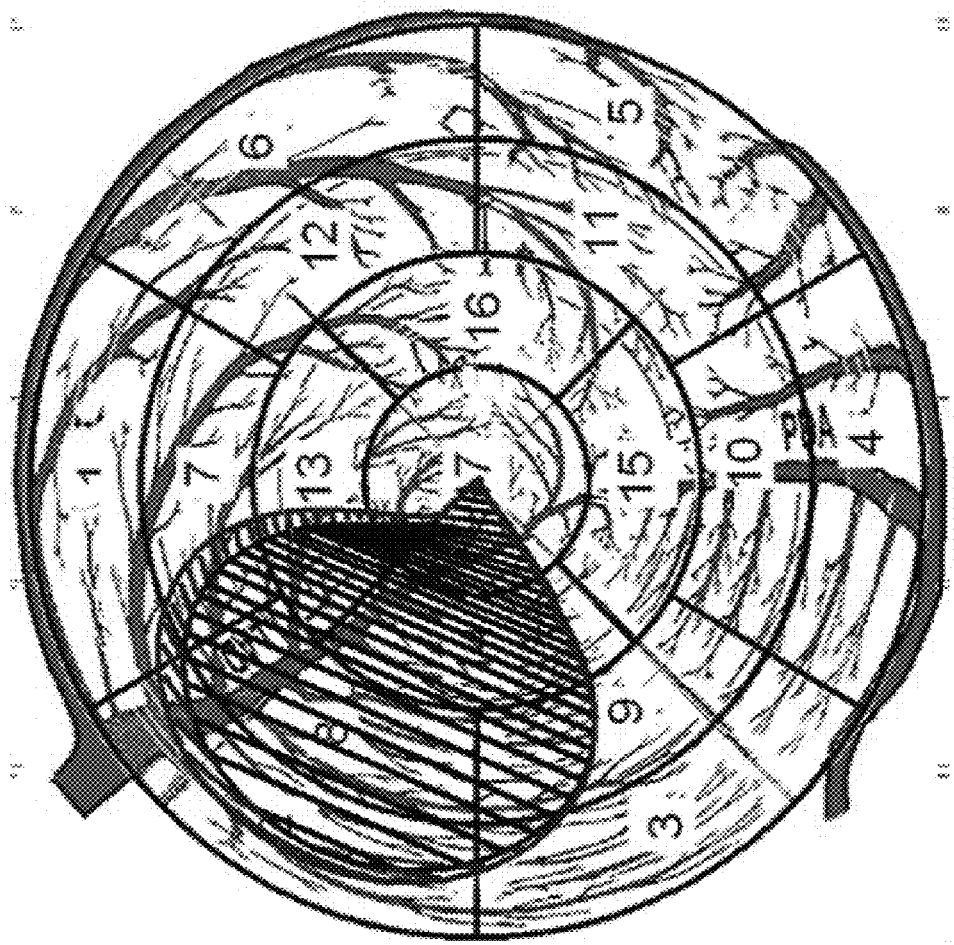
FIG. 14 depicts a Bull's Eye diagram of the left ventricle showing infarct and ischemic areas highlighted in FIG. 13.

For each type of infarction, an ellipse or indicia to visually represent the percent of the LV that is infarcted, according to the rules of Sylvester, is located in the related segments with a center location that is weighted by the infarction, as described for the ischemic case below. The results of the processing by the inventive system and method are illustrated in FIGS. 13 and 14. That is, FIGS. 13 and 14 respectively show how an infarcted area (shaded in black) would appear in a Mercator projection diagram and in a Bulls Eye diagram. A visual cue identifying a percent of LV that is affected enables clinicians, for example, emergency room personnel, to accurately estimate the degree of damage the patient has suffered and what treatment should be provided immediately, if any.

Location of the Ischemic Area on the Heart Diagrams

The location and the size of the ischemic area are very important for determining the degree of risk to the patient. It has been found that the ischemic area is related to the magnitude of the ST vector at the J point. This has been reported in the journals and has been compared to the Aldrich score with good correlation. This relationship for real patient data is shown in FIG. 10B, and a least square fit of the ST vector magnitude to the % LV determined from the Aldrich score can then be used to convert ST magnitude data to % LV. This method has more resolution than the Aldrich score which only uses a binary measure of a lead output. In addition, the ST magnitude evaluates both positive and negative ST deviation so that all leads contribute to the total measurement. In the invention as claimed, the magnitude of the ST vector in each of the leads is determined and then translated to each of the segments.

The sum of the magnitude of the dot products of the segment vectors also is a measure of the ischemic area and if the results of tests of these quantities on patients is made equivalent, the amount of ischemia assigned to each segment is readily found. It has been found that the magnitude determined by the ST magnitude determined from the dower transform of the 12 lead ECG to the X, Y, and Z total vector is highly correlated with the magnitude determine from the segment vectors. This would be suspected since Dower used the Frank Lead vectors in the derivation of his formula.

The amount of ischemia associated with each segment in the display communicates to the clinician the magnitude of the ischemia and where it is located.

The maximum area for a segment is approximately 8 percent of the total area of the heart. If a few segments are less than 8 percent, but they are adjacent, it is logical to join these areas into a combined area that looks like a typical single photon emission computed tomography (SPECT) drawing. This is highlighted in FIGS. 13 and 14, wherein the black (shaded) area is the infarcted area in both the Mercator and the Bulls Eye circle diagram.

To accomplish the location process, the segment signal levels are used to find a weighted location for the center of an ellipse. In the case where the highest levels are in the segments 1 to 6, which has been shown to be LAD, these segments are used to find a horizontal weighted center by comparing segments 1+2+3 to segments 4+5+6. In a similar manner, a vertical weighted center is found by using segments (1+4), segments (2+5) and segments (3+6). Once the center is found, an ellipse is drawn (automatically) with an axis ratio of 3:2 for height to width and an area equal to the percent LV ischemic.

Figure 15A:
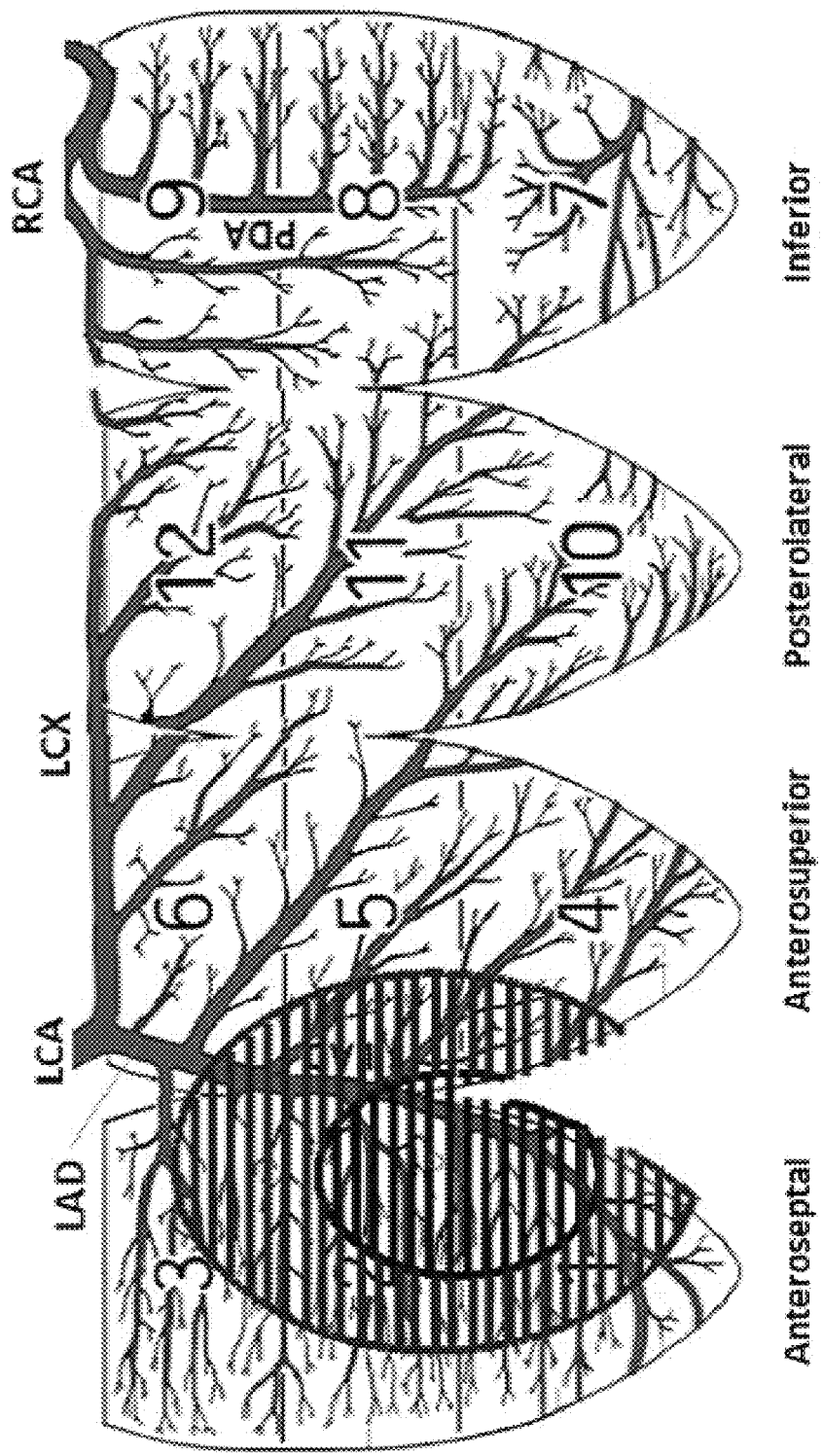
FIG. 15A depicts a Mercator diagram for a patient with both an infarct and ischemia event in the LAD region.
Figure 16A:
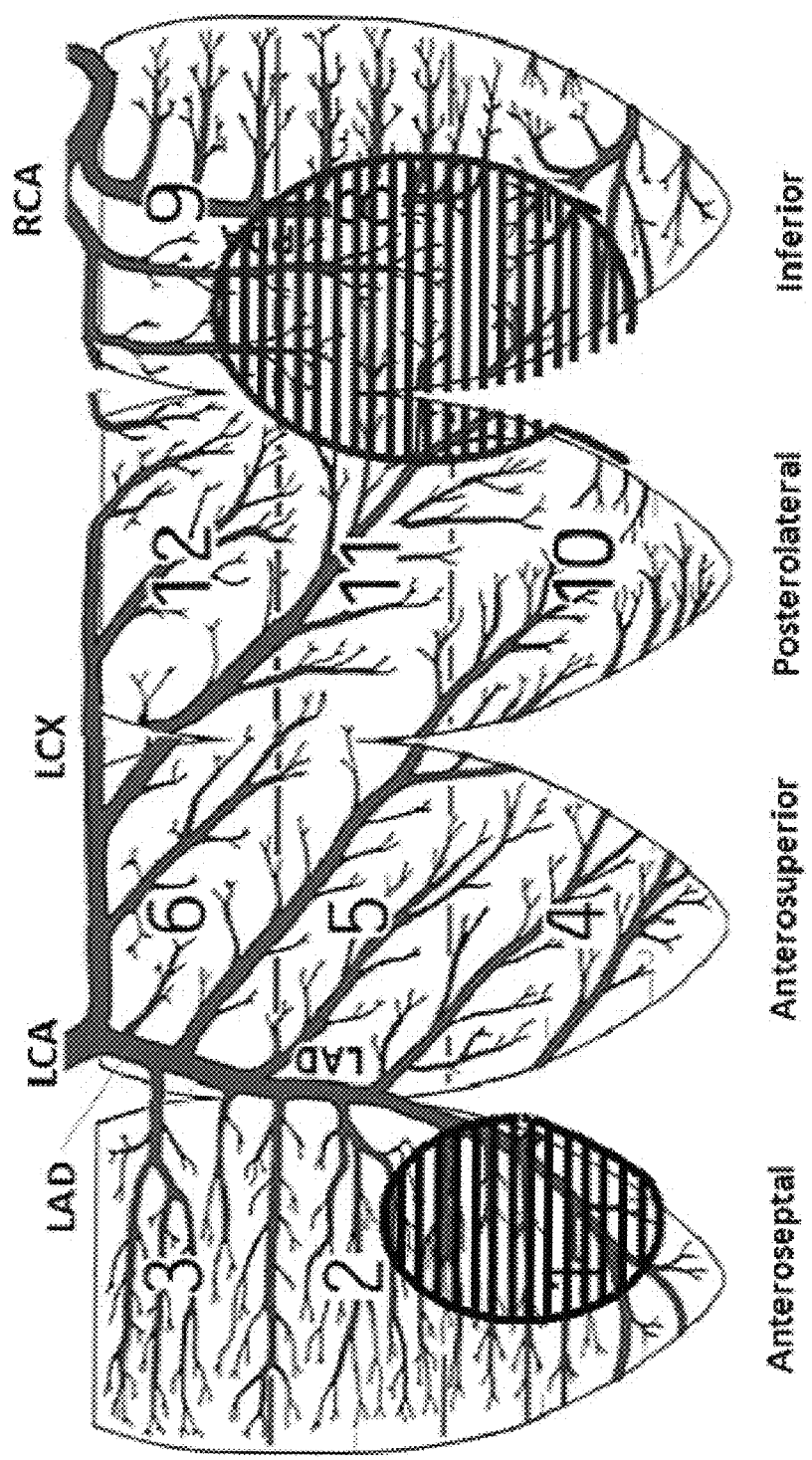
FIG. 16A depicts a Mercator diagram for a patient with an infarct in the LAD region and an ischemia in the RCA region.

This is done in the Mercator projection dimensions and then translated to the circle diagram. FIGS. 15A and 15B shows a diagram of an LAD infarction and an LAD ischemia together. The infarction is shown inside of the ischemia and they are both elliptical in shape. The infarct is computed as 6% of the LV and the ischemia as 23%. The combine area at risk is 29%. A similar method is used for the RCA case where the segments used are 7 to 12. An illustration of an RCA case for Ischemia and an LAD case f or infarction is shown in FIGS. 16A and 16B. The center of the ellipse for their segments were quite different since they represented entirely different areas of the heart If the segments are large in segments 4, 5, 6 along with a larger value for 7, 8, 9 and a smaller value for segments 10, 11, 12 such as in LCX. Then the horizontal weighting would include 3 groups.

This is an entirely new presentation to the cardiologist and should prove to be an extremely valuable tool. That is, the inventive system and method provide the cardiologist with an ability to see the location of the ischemia and the infarction in 2 views of the heart: 1. A Mercator drawing showing all the coronary arteries and 4 quadrants with 3 segments each and 2 A bulls eye drawing with the same information but arranged in a circular format with 17 segments.

The size of the infarction and the ischemia are made in proportion to the size of the damaged area as a % of the LV in a linear relation to the areas on the surface of the Mercator projection. These are then translated to the Bulls eye diagram which is slightly distorted in the outside rings which cover more area than the inside. Showing both the location and the size of the damaged area for the infarct which is not recoverable and the ischemic which is recoverable should be an invaluable aid to making decisions on patient treatment.

Figure 17A:
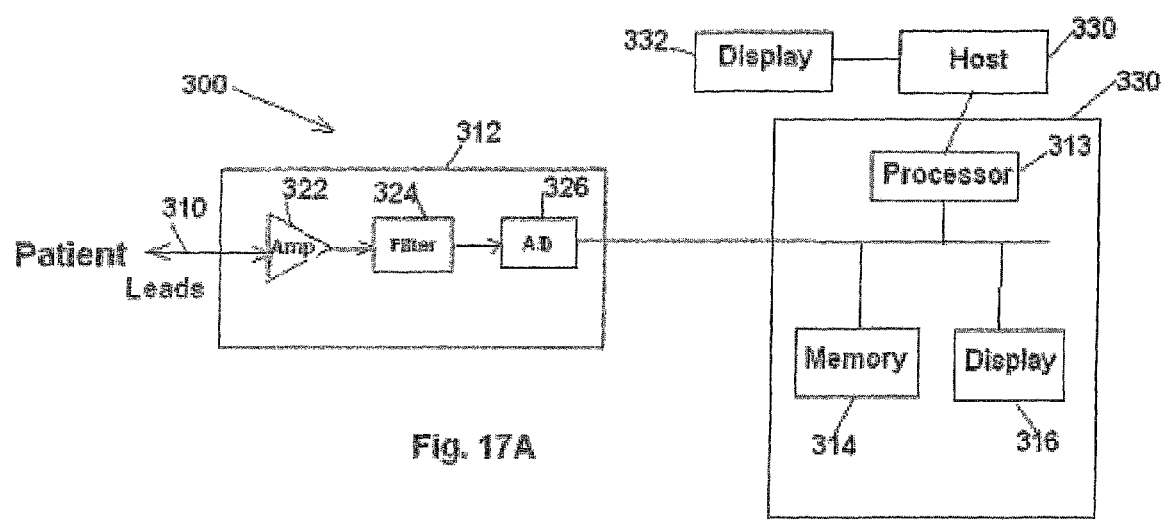
FIG. 17A depicts an apparatus operating according to the inventive principles.
Figure 17B:
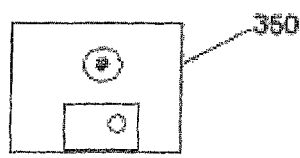
FIG. 17B depicts a non-transitory computer readable medium.

FIG. 17A is a simplified block diagram of an exemplary system 300 for monitoring a patient under test according to the inventive principles. ST-segment resolution according to one embodiment. The system 300 includes a plurality of leads 310 electrically connected to a front end or receiver component 312 that is in communication with a processor 313, a memory device 314, a display device 316, an audio component 318, and an interface component 320. The leads 310 include wires and electrodes configured to attach to a patient (not shown) to detect ECG signals. The receiver 312 may include, for example, an amplification component 322 to amplify the ECG signals detected by the leads 310, a filtering component 324 to eliminate undesirable noise from the ECG signals, and an analog-to-digital (ND) converter 326 to provide converted ECG signals through a system bus 328 to the processor 313.

The processor 313 may include a special purpose processor configured to perform the processes described herein. In another embodiment, the processor 313 is a general purpose processor configured to execute computer executable instructions (e.g., stored in the memory device 314) to perform the processes described herein. In addition, or in other embodiments, the processor 313 may be connected to a host computer 330 having a display device 332. The host computer 330 may include computer executable instructions for performing the processes described herein. The host computer 330 may be used in certain embodiments.

Thus, these aspects of the present invention is directed to a programmed product, comprising a non-transitory signal-bearing storage media tangibly embodying a program of machine-readable instructions executable by a digital data processor incorporating the CPU 112 and hardware above, to perform the method of the invention.

This signal-bearing storage media may include, for example, a RAM contained within the processor 313 or 330, as represented by the fast-access storage for example. Alternatively, the instructions may be contained in another signal-bearing storage media, for example, a magnetic data storage diskette 350 (FIG. 15B), directly or indirectly accessible by the CPU 112.

Whether contained in the diskette 350, or some other computer readable medium, the processor/server 110 comprising CPU 112, or elsewhere, the instructions may be stored on a variety of machine-readable data storage media, such as DASD storage (e.g., a conventional "hard drive" or a RAID array), magnetic tape, electronic read-only memory (e.g., ROM, EPROM, or EEPROM), an optical storage device (e.g. CD-ROM, WORM, DVD, digital optical tape). Other suitable signal-bearing media include memory devices in transmission media and instructions stored in formats such as digital and analog and memory devices in communication links and wireless. In an illustrative embodiment of the invention, the machine-readable instructions may comprise software object code. It should also be obvious to one of ordinary skill in the art that the technique of the present invention could be implemented on a network in a variety of configurations.

Hence, the invention includes a computer program product including a processor and a set of processor readable instructions that when executed by the processor execute method for localizing ischemia in a patient under test and presenting a visual representation of the identified ischemia and/or infarction in a Mercator or Bulls Eye diagram.

As will be evident to persons skilled in the art, the foregoing detailed description and figures are presented as examples of the invention, and that variations are contemplated that do not depart from the fair scope of the teachings and descriptions set forth in this disclosure. The foregoing is not intended to limit what has been invented, except to the extent that the following claims so limit that.

What is claimed is:

1. A system for localizing ischemia in a heart of a patient under test for an ischemic event, comprising:
   an ECG apparatus for connection to a plurality of electrodes adapted to be attached to the patient under test to form a plurality of leads;
   a processor for dividing the patient's heart into a plurality cardiac segments, processing vector signals captured at the plurality of leads for determining normalized vector magnitudes for the leads, determining cardiac segment vectors for each of the plurality of cardiac segments, calculating an output or amount of ischemia for each of the cardiac segments by adding up a contribution to a detected ischemic level for all of the leads in a direction of each of the plurality of cardiac segment vectors at the J point based on the normalized vector magnitudes for the leads, by taking dot products of the lead vectors and the cardiac segment vectors to identify normalized responses for the leads at centers of the cardiac segments to realize the lead's contribution to the detected ischemic level and identifying an ischemic location and amount for each cardiac segment based on a sum of the contributions of all of the leads; and
   a display for presenting the ischemic location and amount calculated by the processor.

2. The system of claim 1, wherein the processing by the processor determines transmural ischemia, indicating that the patient is having a serious heart attack which left unattended will likely create permanent heart muscle damage.

3. The system of claim 1, wherein the normalized vector magnitude for each lead is found by adding the vector magnitudes of each of the lead vectors, and dividing the sum by the number of leads to find an average and dividing the average by each of the individual magnitudes to find the normalized vector magnitude.

4. The system of claim 1, wherein the processor identifies areas of infarction joins the areas of infarction, and presents the joined areas in a Mercator Projection or Bulls Eye diagram in the display.

5. The system of claim 4, wherein the display indicates proximity of the joined areas to a specific coronary artery of the patient under test, said proximity calculated by the processor.

6. The system of claim 1, wherein the processor determines a location and size of an ischemic area and a degree of risk to the patient as a percent of the Left Ventricle or the area at risk (AAR).

7. The system of claim 1, wherein a maximum area for the at least one cardiac segment is 8 percent of a total area of the heart of the patient under test.

8. The system of claim 1, wherein the display indicates proximity of the ischemic location to a specific coronary artery of the patient under test, said proximity calculated by the processor.

9. The system of claim 1, wherein the processor uses the normalized lead vectors to calculate a lead sum vector.

10. The system of claim 1, wherein the processor uses a lead sum vector to localize a point that is central to the detected ischemia by orientation of the lead sum vector in the coordinates of the heart.

\* \* \* \* \*